United States Patent [19]

Muramoto

[11] 4,132,110

[45] Jan. 2, 1979

[54] VIBRATION TYPE LIQUID DENSITY METER

[75] Inventor: Setsuo Muramoto, Musashino, Japan

[73] Assignee: Kabushikikaisha Yokogawa Denki Seisakusho, Tokyo, Japan

[21] Appl. No.: 812,764

[22] Filed: Jul. 5, 1977

[30] Foreign Application Priority Data

Jul. 20, 1976 [JP]  Japan .................................. 51-96313

[51] Int. Cl.² .............................................. G01N 9/00
[52] U.S. Cl. .................................................... 73/32 A
[58] Field of Search ................................ 73/32 A, 32 R

[56] References Cited

U.S. PATENT DOCUMENTS

| 2,943,476 | 7/1960 | Bernstein | 73/32 A |
|---|---|---|---|
| 3,117,440 | 1/1964 | Wilner | 73/32 A |
| 3,728,893 | 4/1973 | Janssen | 73/32 A |
| 3,828,607 | 8/1974 | Janzen et al. | 73/23 |
| 3,983,744 | 10/1976 | Agar | 73/32 A |

FOREIGN PATENT DOCUMENTS

| 2151380 | 4/1973 | Fed. Rep. of Germany | 73/32 A |
|---|---|---|---|
| 41-18530 | 3/1966 | Japan | 73/32 A |
| 460489 | 4/1975 | U.S.S.R. | 73/32 A |

OTHER PUBLICATIONS

Caffin; "Phase Locked Automatic Vibroscope", *Review of Scientific Instruments*, vol. 46, No. 11, pp. 1481–1483, Nov. 1975.

*Primary Examiner*—Stephen A. Kreitman
*Attorney, Agent, or Firm*—Moonray Kojima

[57] ABSTRACT

A vibration type liquid density meter comprising a base, a connector having a mass substantially smaller than said base, two hollow cylindrical elongated pipes each having two ends, one end of each pipe connected to the base, and the other end of each pipe connected to the connector with the pipes disposed substantially parallel to each other and a piezoelectric element attached to the connector for driving the pipes into self excited oscillation at their natural frequency. The liquid to be measured is supplied through the base, pipes and connector and the density of the liquid is measured by the frequency of oscillation with corrections for temperature.

7 Claims, 3 Drawing Figures

VIBRATION TYPE LIQUID DENSITY METER

BACKGROUND OF THE INVENTION

This invention relates to a vibration type liquid density meter which detects the density of a liquid by introducing the liquid into pipes, vibrating the pipes, and the measuring the natural frequency of the vibrating pipes.

One known vibration type liquid density meter comprises a high intensity magnet disposed in the vicinity of a pair of parallely disposed pipes and a current is applied to the pipes to cause their vibration by the Fleming's force thus generated. This device, however, is deficient in many ways. For example, magnetic powder existing in the liquid to be measured is attracted to the magnet and remains in the pipes. This increases the density of the pipes and causes errors in measurements. Moreover, the magnetic powder tends to wear down the pipe walls, and in extreme cases may cause holes in the pipe walls. Furthermore, the magnet and device structure are bulky and inconvenient to use.

Another known device is equipped with a pipe of magnetic material, and the pipe is vibrated by means of an electromagnet. But this device is also deficient in that the typesof liquid which can be measured are limited since a suitable magnetic material of high corrosion resisting property is not yet available. In addition, the device structure is bulky.

There is another known device with a piezoelectric element attached to the middle portion of a pipe. However, this device is deficient in that substantial measurement errors occur since the vibration characteristic of the pipe is varied by attachment of the piezoelectric element to the middle part of the pipe. The lead wires to the piezoelectric element periodically breaks down due to the simultaneous vibration of the piezoelectric element and the pipe.

SUMMARY OF THE INVENTION

An object of the invention is to reduce or eliminate the foregoing and other problems and deficiencies of the prior art.

Another object is to eliminate the damage and wear caused by magnetic powder which may be present in some liquids to be measured.

A further object is to provide a compact, non-bulky vibration type liquid density meter.

A still further object is to provide an improved vibration type density meter which is capable of maintaining stable measurement without breakdown of lead wires and the like.

The foregoing and other objects are attained in the invention which encompasses a vibration type liquid density meter comprising a base having two passageways for liquid to be measured; a connector having a smaller mass than the base and having a passageway therein for said liquid; a pair of parallely disposed hollow cylindrical elongated pipes, each having two ends withone end of each being connected to base in communication with the respective passageway in the base, and the other end of each being connected to the connector in communication with the passageway therein, whereby the liquid to be measured flowing in the circuit comprising the one passageway in the base, one pipe, the passageway in the connector, the other pipe and the other passageway in the base; a piezoelectric element attached to the connector for causing deformation of the connector and the self-excited oscillation of the pipes having liquid therein at their natural frequency. The frequency of oscillation is detected by another piezoelectric element attached to the connector or a capacitive means disposed adjacent to the pipes. The density of the liquid is measured, with correction for other factors, such as temperature, by the rate of vibration of the pipes. A temperature detector may be placed in the passageway of the connector. Auxilliary electronic control and signal processing circuits and recording circuit are provided.

A feature of the invention is the placement of a piezoelectric driving element on the connector which connects similar ends of a pair of parallely disposed similar hollow pipes.

A further feature of the invention is the use of a second piezoelectric element to detect the oscillation of the pipes.

Another feature of the invention is the use of a capacitive measuring device adjacent the pipes to detect the oscillating frequency of the pipes.

A further feature is the placement of the driving piezoelectric element on one surface of the connector and the detecting piezoelectric element on a different part of the connector.

A still further feature is the placement of a temperature detecting device within the passageway of the connector.

DETAILED DESCRIPTION OF PREFERRED EMBODIMENTS

Figure 1:
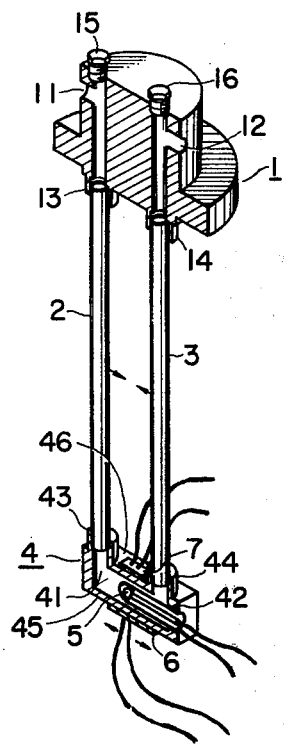
FIG. 1 depicts in sectional view, the mechanical portion of an illustrative embodiment of the invention.

Turning now to FIG. 1, there are depicted a base 1 having a liquid inlet passageway 11, a liquid outlet passageway 12, protrusions 13, 14 formed at the ends of the inlet passageway and outlet passageway, respectively, and blind plugs 15, 16 which are used to close unrequired holes. Connected to base 1 via protrusion 13, 14, respectively, are parallely disposed pipes 2, 3 which have thin walls, are substantially similar to each other in shape and material, and are hollow and cylindrical in shape. The pipes may be of any suitable material such as metal or plastic. Provided at the other end of pipes 2, 3 is a connector 4 having a substantially smaller mass than that of base 1. The connector has a liquid passageway 41 therein and through hole 42 communicated therefrom to the outside. Protrusions 43, 44 formed at the ends of the liquid passageway 41 are connected to pipes 2, 3 respectively. The protrusions of base 1 and of connector 4 hold the pipes tightly and solidly. Disposed within the passageway 41 of connector 4 is a temperature detector 5, used to detect the temperature of the liquid in the passageway 41.

A piezoelectric element 6 which is used to drive pipes 2, 3, is attached to lower surface 45 of connector 4. Another piezoelectric element 7 which is used for detecting vibrations of the pipes 2, 3 is attached to upper surface 46 of connector 4. The two elements are preferably separately mounted, and preferably on separate surfaces of the connector. By mounting the piezoelectric driving elements on the connector, advantageously, accurate and stable measurements of the density of the liquid is obtained.

The base and connectors are preferably of metal, although other suitable materials, such as plastics can be used. The base is shown to be cylindrical, but any suitable shape may be used. It is important, however, that the mass of the base be substantially more than the mass of the connector in order that the connector distortions caused by the piezoelectric driving element 6 can cause self-excited oscillations of the pipes. The connector 4 is shown be be rectangular, and the two piezoelectric units are mounted on opposite surfaces. Other shapes can also be used; however, a rectangular shape is preferred since the distortions caused by the piezoelectric element can be readily effected and transferred to the pipes.

The piezoelectric element 6 functions to apply a tensile force or a compressive force to the surface 45 of connector 4 as indicated by the arrows. When the element 6 generates a tensile force, the surface of connector 4 expands more than the surface 46 so that the connector is deformed to be convex downward. Consequently, the lower ends of pipes 2, 3 are bent in the directions which narrow the space between the middle portions of the pipes as depicted by the arrows between pipes 2, 3. On the other hand, when piezoelectric element 6 generates a compressive force, surface 45 contracts more than surface 46 so that the lower ends of pipes 2, 3 are bent in directions to widen the space between the middle portions of the pipes. Meanwhile, piezoelectric element 7, responsive to the expansion or contraction of the surface 46 of connector 4, produces an output signal. The liquid to be measured flows through inlet passageway 11 of base 1, through pipe 2, through passageway 41 of connector 4, through pipe 3, and through outlet passageway 12 of base 1. The pipes 2, 3 having liquid to be measured therein, oscillate at a frequency related to the density of the liquid as shown hereinbelow. Thus, the measurement of the oscillating frequency of the pipes, with corrections for temperature and other minor factors, will measure the density of the liquid.

Figure 2:
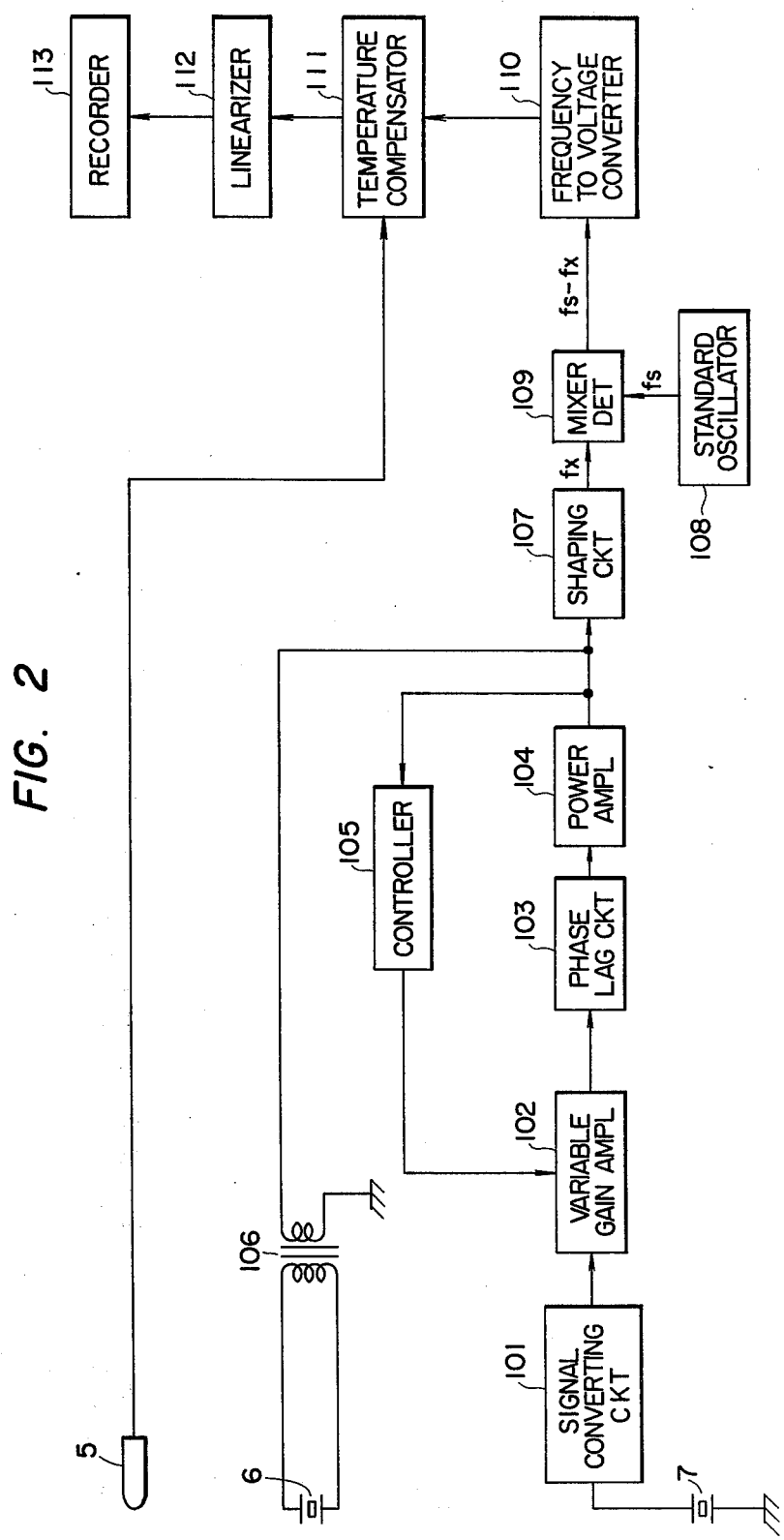
FIG. 2 depicts in block diagram, electrical circuits used in connection with the embodiment of FIG. 1.

FIG. 2 is a block diagram of an illustrative electronic circuit system connected to the device depicted in FIG. 1 and especially to the temperature detector 5 and piezoelectric elements 6 and 7, as depicted. Connected to detecting piezoelectric element 7 is a signal converting circuit 101 for amplifying the output signal from piezoelectric element 7 to a fixed signal level which is then supplied to variable gain amplifier 102. The signal from amplifier 102 is then supplied to a phase lag circuit 103 which causes an output signal which lags 90° in phase behind the output signal of variable gain amplifier 102. The phase lagged signal is then supplied to a power amplifier 104. The output of amplifier 104 is connected to an amplitude controller 105 for regulating the gain of variable gain amplifier 102 to maintain constant the output amplitude of power amplifier 104. The output voltage of power amplifier 104 is increased by transformer 106 connected to the output of amplifier 104, and applied to piezoelectric element 6. Shaping circuit 107 receives the output signal of power amplifier 104 and after shaping, applies it to mixer 109. A standard oscillator 108 produces an output signal of a fixed frequency (fs). A mixer detector 109 produces an output signal of a frequency (fs - fx) which is the difference between the output frequency (fs) of the standard oscillator 108 and the output frequency (fx) of the shaping circuit 107. This difference signal is then applied to frequency-to-voltage converter 110 for producing an output signal of a direct current voltage proportional to the output frequency of mixer detector 109. A temperature compensator 111 is connected to temperature detector 5 and acts to effect temperature compensation with respect to the output signal of frequency-to-voltage converter 110 in accordance with the output signal of temperature detector 5. A linearizer 112 receives signals from the comensator 111 and converts it to a signal proportional to density. The signal is then supplied to a recorder 113. The recorder may also be connected to a visual display. Each of these circuit components and their functions are known in the art and can be readily obtained.

The liquid density meter using the above-described circuit configuration operates in the following manner. The vibration of connector 4 which moves by nature of oscillation of pipes 2, 3, is detected by piezoelectric element 7 and is converted into an electric signal, which is then amplified by signal converting circuit 101, and supplied to variable gain amplifier 102. The phase of the signal thus amplified is delayed 90° by phase lag circuit 103. Subsequently, the lagging signal is amplified by power amplifier 104. After amplification and 180° phase shift by transformer 106, the signal is applied to piezoelectric element 6, thereby driving connector 4 to vibrate pipes 2, 3. Then, the pipes 2, 3 filled with liquid to be measured, are activated to vibrate at their natural frequency. At the occurence of natural frequency vibration, the phase lag between piezoelectric element 6 and piezoelectric element 7 becomes 90°. Consequently, the connector driving closed circuit including the piezoelectric elements 6 and 7 are excited to oscillate, hence vibrating the pipes 2, 3 in a fixed amplitude regulated by amplitude controller 105. The frequency of the self-excited oscillation of pipes 2 and 3 (i.e. the natural frequency of pipes filled with the liquid) directly becomes the output frquency (fx) of shaping circuit 107. The relationship between this output frequency (fx) and the liquid density ($\rho x$) is represented by the following equation:

$$fx = \frac{C}{4l^2} \cdot \sqrt{\frac{E}{e1}} \sqrt{\frac{D_1^2 + D_2^2}{1 + \frac{ex}{e1} \cdot \frac{D_2^2}{D_1^2 - D_2^2}}}$$

wherein
C = constant
l = effective length of pipe 2 (see FIG. 1)
E = longitudinal elasticity modulus of pipe 2.
$\rho_1$ = density of pipe 2
$D_1$ = outer diameter of pipe 2.
$D_2$ = inner diameter of pipe 2.

The difference (fs − fx) between the output frequency (fx) of shaping circuit 107 and the output frequency (fs) of the standard oscillator 108 is obtained from mixer detector 109. Then it is converted to a d-c voltage by frequency to voltage converter 110. The mixer detector 109 serves to extend the changing rate of the frequency fix.

Generally the density of a liquid has a temperature coefficient, and the longitudinal elasticity modulus of pipes 2, 3 also has a temperature coefficient. Thus, the temperature compensator 111 converts the output signal from a frequency to voltage converter 110 to a signal relativeto the density based on a reference temperature and signal from temperature detector 5. The output signal of temperature compensator 111 is converted by the linearizer 112 to a signal proportional to the density based on the reference temperature, and then is recorded by recorder 113.

Figure 3:
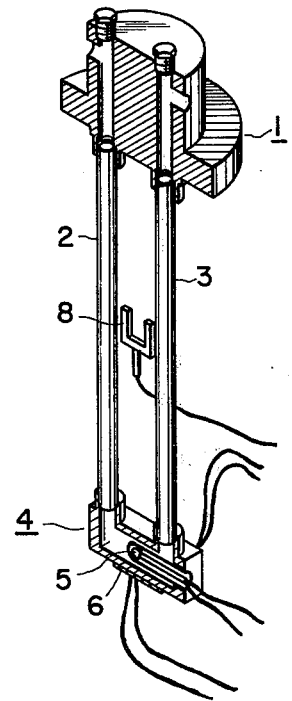
FIG. 3 depicts in sectional view, another illustrative embodiment using a capacitive detecting element.

In the embodiment fo FIG. 1, the vibration of pipes 2, 3 is detected by piezoelectric element 7. However, it is also possible to use a capacitance electrode 8 instead of the piezoelectric element 7 as illustrated in FIG. 3, wherein the same reference numbers for similar parts are used as in FIG. 1. The vibration of pipes 2 and 3 is detected by the capacitance change between pipes 2, 3 and the electrode 8. Other suitable means may be used for detecting the vibration of pipes 2, 3. As for the electric circuits connected to the mechanical parts of FIG. 1 and shown in FIG. 2, the signal converting circuit 101 may be modified to enable detection by capacitance change and to change such capacitance change to a voltage change.

In the liquid density meter of this invention, wherein vibration of pipes is caused by piezoelectric driving element attached to the connector, no magnetic powder remains in the pipes. Thus, advantageously, the invention prevents damage and wear to the pipes and excludes any measurement errors resulting from the presence of residual magnetic powder. Also, advantageously, since the piezoelectric driving element is attached to a separate connector, and not to the middle portion of the pipes as in the prior art, measurement errors are minimized. Also, the device is structurally of small dimensions because magnets and the like are not used. Furthermore, since the piezoelectric elements are attached to the connector, which is nearly stationary in the present invention, there is less likelihood of breakdown of lead wires to the piezoelectric element. Thus, advantageously, all of the disadvantages and deficiences of the prior art have been overcome.

The foregoing description is illustrative of the principles of the invention. Numerous other variations and modifications thereof would be apparent to the worker skilled in the art. All such variations and modifications are to be considered to be within the spirit and scope of the invention.

What is claimed is:

1. A liquid density meter comprising
(A) a base having a passageway for flow of liquid to be measured;
(B) a pair of hollow, cylindrical, elongated pipes of substantially similar measurements and physical properties, disposed substantially parallel to each other;
(C) a connector having a passageway therein for flow of said liquid, and being of a mass substantially smaller than said base;
(D) means for connecting one end of each pipe to said base in communication with said passageway therein;
(E) means for connecting the other end of each pipe to said connector in communication with said passageway therein;
(F) piezoelectric means attached to said connector for applying a force substantially perpendicular to said pipes for causing deformation of said connector and the oscillation of said pipes; and
(G) means for detecting the said oscillations of said pipes, wherein said detecting means includes a temperature detector disposed within said connector, and circuit means for compensating the detected oscillation frequency in relation to density of the liquid for temperature.

2. The meter of claim 1, wherein said means for detecting comprises a second piezoelectric means attached to a different part of said connector.

3. The meter of claim 1, wherein said means for detecting comprises a capacitive means disposed adjacent to said pipes to detect capacitive changes relative to said oscillation of said pipes.

4. A vibration type liquid density measuring system comprising
(A) a device comprising
(i) a base of suitable mass and having a pair of passageway therein,
(ii) a pair of hollow, cylindrical, elongated pipes of substantially similar physical properties, disposed substantially parallel to each other,
(iii) a connector of substantially smaller mass than said base, and having a passageway therein,
(iv) temperature detecting means disposed within said passageway of said connector,
(v) means for connecting one end of each pipe to said base in communication with respective said passageways therein,
(vi) means for connecting the other end of each pipe to said connector in communication with said passageway therein, whereby liquid to be measured flows in a circuit comprising one of said passageways in said base, one of said pipes, said passageway in said connector, the other of said pipes, the other of said passageways in said base,
(vii) piezoelectric driving means attached to said connector for applying a force substantially perpendicular to said pipes for causing its deformation and the oscillation of said pipes filled with liquid at their natural frequency, and
(viii) means for detecting the oscillation of said pipes; and
(B) circuit means comprising
(i) means connected to said means for detecting, for converting and amplifying signals therefrom,
(ii) means for obtaining the frequency of the signal from said means for detecting,
(iii) means for comparing the frequency of the detected signal with a standard frequency and generating a difference singal therefrom,
(iv) means for converting the difference signal to a voltage signal,
(v) means connected to said temperature detecting means for compensating the voltage signal for temperature,
(vi) means for converting the temperature compensated signal into a linear signal, and
(vii) means for recording said linear signal.

5. The system of claim 4, wherein said means for detecting comprises a piezoelectric element.

6. The system of claim 4, wherein said means for detecting comprises a capacitive of detecting element.

7. The system of claim 4, wherein said circuit means takes the signal from said amplifier, and after phase lag supplies it to a transformer and thereafter to said piezoelectric driving means.

* * * * *